United States Patent
Singh (10) Patent No.: US 10,071,344 B2
(45) Date of Patent: Sep. 11, 2018

(54) REDUCTANT DOSING CONTROL USING PREDICTION OF EXHAUST SPECIES IN SELECTIVE CATALYTIC REDUCTION

(71) Applicant: Nishant Singh, Bothell, WA (US)

(72) Inventor: Nishant Singh, Bothell, WA (US)

(73) Assignee: PACCAR Inc, Bellevue, WA (US)

( * ) Notice: Subject to any disclaimer, the term of this patent is extended or adjusted under 35 U.S.C. 154(b) by 249 days.

(21) Appl. No.: 14/887,279

(22) Filed: Oct. 19, 2015

(65) Prior Publication Data

US 2017/0106338 A1    Apr. 20, 2017

(51) Int. Cl.
*G01N 33/00* (2006.01)
*B01D 53/94* (2006.01)

(52) U.S. Cl.
CPC ..... *B01D 53/9495* (2013.01); *B01D 53/9409* (2013.01); *B01D 53/9431* (2013.01); *G01N 33/0037* (2013.01); *G01N 33/0054* (2013.01); *B01D 2257/404* (2013.01)

(58) Field of Classification Search
CPC .... F01N 2560/026; F01N 3/208; F01N 11/00; F01N 11/002; F01N 2550/00; F01N 2560/14; F01N 2900/0601; F01N 2900/1621; B01D 53/9431; B01D 53/30; B01D 53/9409; B01D 53/9495; F02D 41/146
See application file for complete search history.

(56) References Cited

U.S. PATENT DOCUMENTS

| | | |
|---|---|---|
| 7,140,874 B2 | 11/2006 | Ingalls, Jr. |
| 8,140,248 B2 | 3/2012 | Mehendale |
| 8,230,677 B2 | 7/2012 | Devarakonda |
| 8,626,451 B2 | 1/2014 | Wang |
| 8,793,977 B2 | 8/2014 | Kaemingk |

(Continued)

OTHER PUBLICATIONS

Surenahalli, H. S., et al., "Extended Kalman Filter Estimator for NH3 Storage, NO, NO2 and NH3 Estimation in a SCR," No. 2013-01-1581, SAE International, Apr. 2013.

(Continued)

*Primary Examiner* — Dennis Michael White
*Assistant Examiner* — Bryan T Kilpatrick
(74) *Attorney, Agent, or Firm* — Christensen O'Connor Johnson Kindness, PLLC; Ryan Dodge; John Denkenberger (57) ABSTRACT

A system and related method for controlling reductant dosing in a selective catalyst reduction system includes a chamber containing a catalyst, and a controllable reductant dosing system that includes a controllable injector connected to a reservoir of reductant, and a controller that obtains inlet exhaust temperature, speed, and composition information, for example, from one or more sensors in the exhaust stream. The controller solves a set of coupled equations comprising (i) one-dimensional, steady ammonia mass balance equations and (ii) one-dimensional, steady species mass transfer equations, to calculate a one-dimensional distribution of ammonia storage in the catalyst and a one-dimensional distribution of exhaust species concentrations through the SCR system including a concentration of ammonia and a concentration of one or more nitrogen oxides at the SCR outlet; and uses the solution to control the injector. The method has been found to anticipate ammonia and NOx slip.

20 Claims, 5 Drawing Sheets

(56) References Cited

U.S. PATENT DOCUMENTS

| | | |
|---|---|---|
| 8,800,529 B2 | 8/2014 | Wickstone |
| 8,820,050 B2 * | 9/2014 | Dubkov ............... F01N 3/208 60/274 |
| 8,966,880 B2 | 3/2015 | Gerty |
| 2007/0080075 A1 | 4/2007 | Wang |
| 2009/0242401 A1 | 10/2009 | Horisaka |
| 2010/0101214 A1 * | 4/2010 | Herman ............... F01N 3/208 60/277 |
| 2010/0107609 A1 * | 5/2010 | Parmentier ........... B01D 53/90 60/286 |
| 2011/0146606 A1 | 6/2011 | Cannella |
| 2012/0060469 A1 | 3/2012 | Gady |
| 2013/0019588 A1 | 1/2013 | Richardson |
| 2013/0104638 A1 | 5/2013 | Takahashi |

OTHER PUBLICATIONS

Twigg, M. V., "Urea-SCR Technology for deNOx After Treatment of Diesel Exhausts," Johnson Matthey Technology Review 59(3):221-232, Jul. 2015.

\* cited by examiner

REDUCTANT DOSING CONTROL USING PREDICTION OF EXHAUST SPECIES IN SELECTIVE CATALYTIC REDUCTION

BACKGROUND

Lean burning internal combustion engines, including modern diesel engines, produce significant nitrogen oxides (NOx). Because of health risks associated with NOx, the U.S. Environmental Protection Agency places regulatory limits on acceptable levels of NOx emissions.

To reduce environmental impacts and to meet regulatory air pollution limits for diesel engines, manufacturers of diesel engines are adopting exhaust after-treatment systems that significantly reduce or eliminate undesirable emissions. After-treatment systems, for example, diesel particulate filters, such as catalyzed soot filters, trap diesel particulate matter and reduce emissions. Selective catalytic reduction (SCR) is a technology for reducing NOx in engine exhaust. SCR is the leading technology being used to meet emission regulations for 2010 and beyond. While NOx encompasses a number of different compounds, for practical applications it is frequently enough to consider only NO and $NO_2$, and NOx is sometimes used to refer specifically to these compounds.

SCR systems catalytically react exhaust stream NOx with other compounds to produce diatomic nitrogen and water. A typical SCR system receives engine exhaust into a chamber containing a suitable catalyst. Small quantities of a reductant are injected into the exhaust upstream of a catalyst. NOx reductants include, for example, anhydrous ammonia, aqueous ammonia, or urea. The reductant, cooperatively with the catalyst, reduces NOx into more benign compounds. SCR systems used in modern diesel trucks use a reductant referred to as diesel exhaust fluid (DEF), and standardized as ISO 22241. DEF is an aqueous urea solution of 32.5% high purity urea and 67.5% deionized water. DEF is metered or injected into the exhaust stream and thermally decomposes to produce ammonia, which, in the presence of the catalyst reacts with NOx in the exhaust, producing nitrogen and water.

Optimally, the quantity of reductant injected is sufficient to react substantially all of the NOx in the exhaust. However, if too much reductant is injected into the exhaust, excess reductant, e.g., ammonia, will exit the SCR without reacting. Reductant that exits the SCR without reacting with NOx is referred to generally as ammonia slip. Typically, an ammonia slip catalyst is provided downstream, to prevent ammonia from exiting the tail pipe. The ammonia slip is an undesirable emission and is wasteful of the consumable reductant. On the other hand, if too little reductant is injected into the SCR then undesirable levels of unreacted NOx will exit the SCR. NOx that exits the SCR is generally referred to as NOx slip. In an optimal SCR system ammonia slip and NOx slip are minimized.

The composition and temperature of the incoming exhaust stream varies, and optimal reductant dosing is therefore a transient target. For example, in diesel engines used for Class 8 vehicles the engine operating parameters change due to changing engine load, changes in environmental conditions, and the like. The optimal rate of reductant dosing varies significantly during operation of the engine. Therefore reductant dosing is typically actively controlled, based on measured conditions, for example, by reducing the dosing if ammonia slip is detected or increasing the dosing if NOx slip is detected. It would be beneficial to predict the onset of ammonia slip and NOx slip, and to adjust reductant dosing to prevent (or mitigate) slip.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

A method for controlling reductant dosing to an exhaust stream for a selective catalytic reduction (SCR) system having an inlet, an outlet, an SCR catalyst, a controllable reductant injector, a reservoir of reductant fluidly connected to the reductant injector, and a controller in signal communication with the reductant injector is disclosed. The method includes obtaining an exhaust stream temperature upstream of the SCR catalyst, obtaining a speed of the exhaust stream entering the SCR system, and obtaining a concentration of one or more nitrogen oxides entering the SCR system. The controller is operated to (i) calculate a one-dimensional temperature profile and a one-dimensional exhaust stream velocity profile through the SCR system using the exhaust stream temperature entering the SCR system and the speed of the exhaust stream entering the SCR system; (ii) solve a set of coupled equations comprising (a) one-dimensional, steady ammonia mass balance equations and (b) one-dimensional, steady species mass transfer equations, to calculate a one-dimensional distribution of ammonia storage in the catalyst and a one-dimensional distribution of exhaust species concentrations through the SCR system including a concentration of ammonia and a concentration of one or more nitrogen oxides at the SCR outlet; and (iii) control the reductant injector, wherein the injector is controlled based on the calculated concentration of ammonia and the calculated concentration of one or more nitrogen oxides at the SCR outlet.

In an embodiment the upstream exhaust stream temperature is obtained from a first sensor module in the exhaust stream, and further includes the step of obtaining a downstream exhaust stream temperature from a second sensor module, wherein the one-dimensional temperature profile is calculated by interpolating between the upstream exhaust stream temperature and the downstream exhaust stream temperature.

In an embodiment the one-dimensional exhaust stream temperature profile is obtained by solving a one-dimensional energy equation, and the concentration of nitrogen oxides entering the SCR system is obtained from a sensor module in the exhaust stream upstream of the SCR catalyst, for example, with the sensor module measuring the concentration of the nitrogen oxides, such as NO and $NO_2$.

In an embodiment the speed of the exhaust stream entering the SCR system is calculated from an exhaust flow rate and the exhaust stream temperature upstream of the SCR catalyst.

In an embodiment the one-dimensional, steady ammonia mass balance equations model adsorption, desorption, and storage of ammonia on the SCR catalyst.

In an embodiment the controller controls the reductant injector also based on the rate of change of the calculated concentration of ammonia and the calculated concentration of one or more nitrogen oxides at the SCR outlet.

A system for controlling the dosing of reductant in a selective catalytic reduction (SCR) system for a diesel engine is disclosed. The system includes a chamber having an inlet and an outlet, an SCR catalyst disposed in the chamber, a controllable injector configured to inject reductant into the chamber, a reservoir for SCR reductant fluidly connected to the injector, and an upstream sensor module positioned to intercept an exhaust stream from the diesel engine upstream of the chamber. A controller is in signal communication with the upstream sensor module and with the injector, and is configured to (i) receive an upstream exhaust stream temperature and a concentration of one or more nitrogen oxides in the exhaust stream from the upstream sensor module; (ii) calculate a speed of the exhaust stream entering the SCR system; (iii) calculate a one-dimensional temperature profile and a one-dimensional exhaust stream velocity profile through the SCR system using the exhaust stream temperature entering the SCR system and the speed of the exhaust stream entering the SCR system; (iv) solve a set of coupled equations comprising (a) one-dimensional, steady ammonia mass balance equations and (b) one-dimensional, steady species mass transfer equations, to calculate a one-dimensional distribution of ammonia storage in the catalyst and a one-dimensional distribution of exhaust species concentrations through the SCR system including a concentration of ammonia and a concentration of one or more nitrogen oxides at the SCR outlet; and (v) control the reductant injector, wherein the injector is controlled based on the calculated concentration of ammonia and the calculated concentration of one or more nitrogen oxides at the SCR outlet.

In an embodiment the upstream sensor module is disposed at the inlet to the chamber.

In an embodiment the system also includes a downstream sensor module disposed at the outlet to the chamber and is in signal communication with the controller, and the controller obtaining a downstream exhaust stream temperature from the downstream sensor module, and calculates the one-dimensional temperature profile by interpolating between the upstream exhaust stream temperature and the downstream exhaust stream temperature.

In an embodiment the one-dimensional exhaust stream temperature profile is obtained by solving a one-dimensional energy equation.

In an embodiment the upstream sensor module measures the concentration of a plurality of nitrogen oxides, for example, the concentration of NO and $NO_2$.

In an embodiment the speed of the exhaust stream entering the SCR system is calculated from an exhaust flow rate and the upstream exhaust stream temperature.

In an embodiment the one-dimensional, steady ammonia mass balance equations model adsorption, desorption, and storage of ammonia on the SCR catalyst.

In an embodiment the controller controls the reductant injector also based on the rate of change of the calculated concentration of ammonia and the calculated concentration of one or more nitrogen oxides at the SCR outlet.

In an embodiment the selective catalytic reduction (SCR) system is configured to be installed on the diesel engine of a Class 8 truck.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Embodiments of the present invention will now be described with reference to the drawings, where like numerals correspond to like elements. The present disclosure is generally directed to methods and systems for controlling the rate, amount, and/or timing of dosing of reductant into the exhaust stream upstream of the catalyst in a selective catalytic reduction system (SCR) of a diesel engine. Typically, the reductant is diesel engine fluid (DEF). The DEF injection is controlled to minimize the release of NOx without releasing significant unreacted reductant. More particularly, methods and systems are disclosed that use measured and/or calculated operating parameters of the engine and/or exhaust system (e.g., exhaust temperature (T), velocity/speed (V), etc.), and a control system running a numerical model of the SCR system to anticipate slip, and using the anticipated slip information to control the dosing or rate of injection of reductant to the SCR system. The model anticipates the occurrence of ammonia slip and NOx slip, such that the dosing can be adjusted to prevent or mitigate ammonia slip and NOx slip before significant slippage occurs.

In a current embodiment a one-dimensional model calculates a temperature distribution though the SCR, the species mass transfer due to NOx reactions within the SCR, the adsorption and desorption of ammonia on the catalyst in the SCR, and the ammonia mass balance to predict rapid changes in the concentrations of ammonia and/or NOx at the outlet of the SCR. The model predicts NOx slip and ammonia slip sufficiently early to allow the control system to adjust the reductant dosing to avoid or greatly reduce the predicted slippage.

It should also be understood that the following description regarding models, controllers or other computing devices for implementing the models, etc., are presented largely in terms of logic and operations that may be performed by conventional electronic components. These electronic components, which may be grouped in a single location or distributed over a wide area, may generally include processors, memory, sensors, etc. It will be appreciated by one skilled in the art that the logic described herein may be implemented in a variety of configurations, including software, hardware, or combinations thereof. The hardware may include, but is not limited to, analog circuitry, digital circuitry, processing units, application specific integrated circuits, and the like. In circumstances where the components are distributed, the components are accessible to each other via communication links.

Although exemplary embodiments of the present disclosure will be described hereinafter with reference to over the road vehicles, particularly diesel-powered, heavy duty trucks, it will be appreciated that aspects of the present disclosure have wide application and, therefore, may be suitable for use with many other types of vehicles that include a urea or other nitrogen-oxides reductant injection system for treating nitrogen oxides emissions in an exhaust stream, such as automobiles, recreational vehicles, boats, etc. Examples of the subject matter of the present disclosure may find other applications, such as the treatment of exhaust streams of stationary or portable generators, etc.

In the following description, numerous specific details are set forth in order to provide a thorough understanding of exemplary embodiments of the present disclosure. It will be apparent to one skilled in the art, however, that many embodiments of the present disclosure may be practiced without some or all of the specific details. In some instances, well-known process steps have not been described in detail in order to not unnecessarily obscure various aspects of the present disclosure. Further, it will be appreciated that embodiments of the present disclosure may employ any combination of features described herein.

Figure 1:
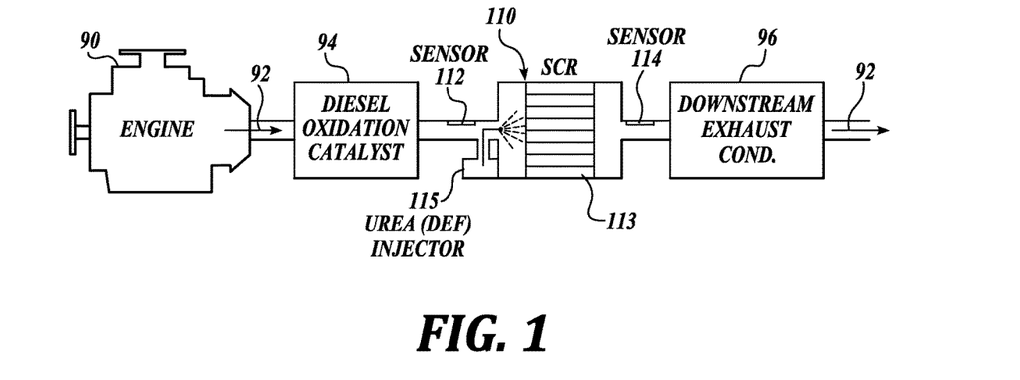
FIG. 1 is a diagram showing a diesel engine with an SCR system in accordance with the present invention.

A system diagram illustrating a diesel engine 90 with an exhaust conditioning system 100 including a selective catalytic reduction (SCR) system 110 in accordance with the present invention, is shown in FIG. 1. The exemplary system 100 receives an exhaust stream 92 from the diesel engine 90. The exhaust stream 92 may pass through one or more upstream exhaust conditioning systems. A diesel oxidation catalyst (DOC) 94 is illustrated in FIG. 1 upstream of the SCR system 110. The DOC 94 oxidizes NO to NO2, thereby significantly increasing the NO2/NOx ratio, and reducing the amount of reductant required. Other upstream exhaust conditioning systems are known in the art, for example, a diesel oxidation catalyst (DOC) 94 may be used upstream of the SCR system 110 some applications, as discussed above. The exhaust stream 92 is then directed to the SCR system 110, for reduction of nitrogen oxides (NOx) in the exhaust stream 92. The exhaust stream 92 exiting the SCR system 110 may optionally be further processed through further downstream conditioning systems 96. For example, the downstream conditioning systems 96 may include systems for further reducing NOx, for eliminating ammonia, and/or for removing particulate matter from the exhaust stream 92.

The SCR system 110 comprises a chamber 111 containing a catalyst 113. The catalyst may be configured, for example, with a plurality of axial channels generally aligned with the flow direction, e.g., in a honeycomb configuration. A controllable injector 115 injects the NOx reductant solution, e.g., DEF, into the exhaust stream 92 upstream of the catalyst 113. Ammonia from the injected DEF adsorbs onto the surface of the catalyst 113. A portion of the ammonia catalytically reacts with exhaust stream NOx, some of the ammonia is stored on the catalyst 113, and the remainder of the ammonia desorbs from the catalyst 113 back into the exhaust stream 92.

Suitable catalytic materials are well known in the art. For example, SCR catalysts may comprise a carrier, typically ceramic materials such as titanium oxide, and an active catalytic component, for example, oxides of base metals, zeolites, or various precious metals.

The SCR system 110 may include an upstream sensor module 112 that detects and measures properties of the exhaust stream 92 at the entrance so the SCR system 110 and/or a downstream sensor module 114 that senses properties of the exhaust stream 92 at the exit to the SCR system 110. For example, in a particular embodiment the upstream sensor module 112 includes an exhaust stream flow rate or velocity sensor and a temperature sensor, and the downstream sensor module 114 includes a NOx sensor and a temperature sensor. For example, the flow speed may be calculated from the exhaust flow rate and temperature information. In one embodiment the flow rate information is available from the model and the temperature is obtained from a sensor. Other sensor configurations are possible, as will be apparent to persons of skill in the art. For example, a temperature sensor and flow sensor may be located at any convenient location upstream and downstream of the SCR 113. The NOx sensor may measure concentrations of NO, $NO_2$, and/or all NOx.

As discussed above, it is desirable to minimize ammonia slip (ammonia that exits the SCR system 110 without reacting with NOx). Ammonia slip is a waste of the consumable DEF and can be detrimental to biological entities. Ammonia may also produce an unpleasant odor. It is also desirable to remove as much of the NOx from the exhaust stream as is reasonably possible. In order to optimize the efficiency of the SCR system 110, the rate of injection of the DEF is actively controlled.

Figure 2:
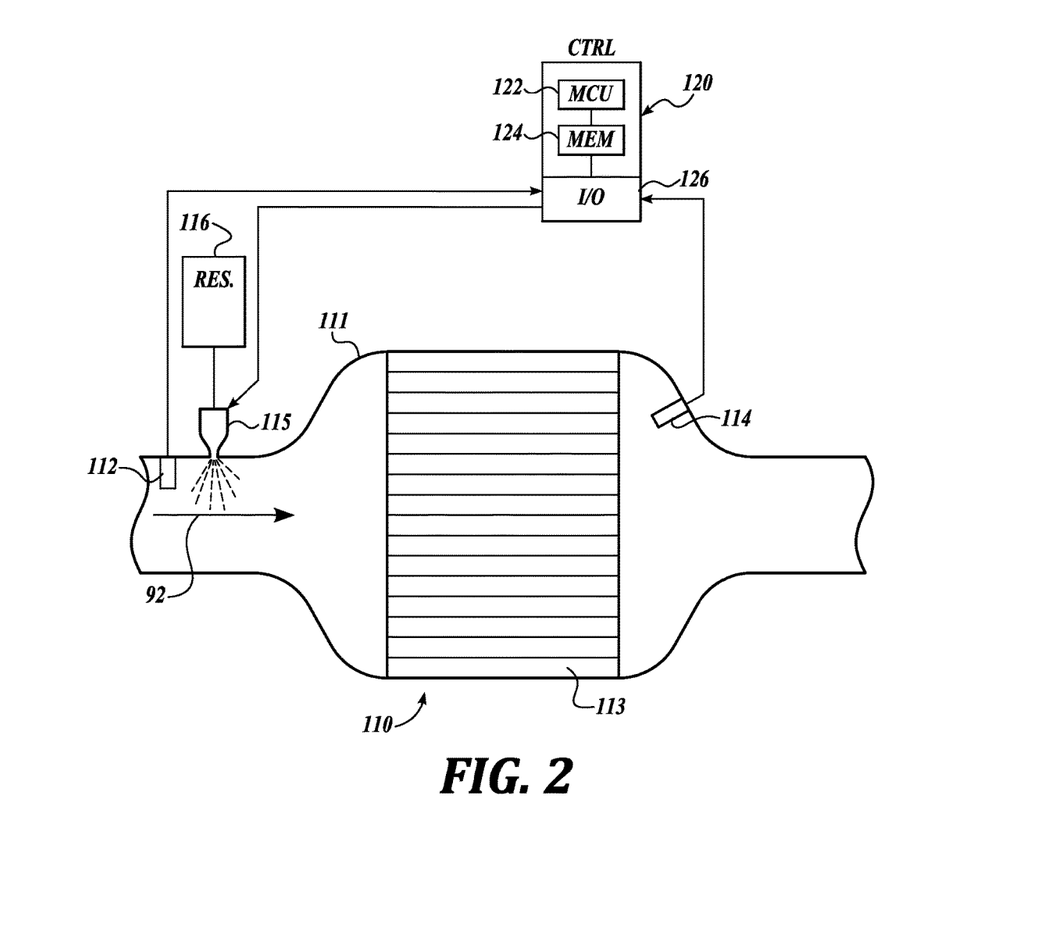
FIG. 2 is a diagram showing more details of the SCR system shown in FIG. 1.

FIG. 2 is a schematic view of the SCR system 110. The SCR system 110 includes the doser or injector 115 that injects reductant from a reservoir 116 into the exhaust stream 92 upstream of the catalyst chamber 111. The DEF thermally releases ammonia into the exhaust stream 92. The exhaust stream 92 transports the entrained ammonia to the catalyst 113, wherein at least a portion of the ammonia is adsorbed onto the catalyst 113.

The SCR system 110 further includes a controller 120. The controller 120 executes one or more models and uses the results to control the injector 155 to optimize the dosing rate. The model may include a number of different modules, for example, a wall wetting module, a crystallization module, or the like, as are known in the art. See, for example, U.S. Pat. No. 8,793,977, which is hereby incorporated by reference.

A dosing model is disclosed herein that anticipates the occurrence of ammonia slip and NOx slip, such that the injector can be adjusted prior to the onset of slippage. The controller 120 includes components capable of receiving input signals from one or more sensors, etc., processing and/or storing the input signals, retrieving data from memory or other systems of the vehicle, and generating appropriate control signals for output to the injector 115. In the present embodiment the controller receives information from the sensors 112, 114.

In this exemplary embodiment the controller 120 includes a processor 122 and memory 124 with a random access memory, an electronically erasable, programmable read only memory ("EEPROM") and any other suitable data storage means. Stored as executable instructions in memory are program modules, which can include routines, programs, objects, components, data structures, etc., that perform particular tasks or implement particular abstract data types. The controller 120 is connected by an input/output (I/O) interface 126 to sensor modules 112, 114. Other systems, devices, and/or controllers of the vehicle not illustrated but known in the art, such as an engine control unit (ECU), transmission control unit (TCU), etc., can also be connected to the I/O interface 126 via a vehicle wide network or other communication link. In that regard, the controller 120 may receive other vehicle or system data, such as vehicle speed data, engine speed data, fuel consumption data, humidity and/or dew point data, ambient temperature data external to the exhaust system, etc. Such sensors are known, and the selection of appropriate sensors is well within the skill in the art.

The controller 120 is operatively connected to the injector 115, to control the rate of delivery of reductant to the exhaust stream 92. It will be appreciated that the NOx reductant injector 115 in some embodiments may inject NOx reductant in intermittent bursts depending on the reductant demand indicated by the controller 120, to achieve a desired dosing. For example, if the controller 120 indicates that more reductant is needed, the controller 120 instructs the reductant injector 115 via appropriate control signals to inject an amount of NOx reductant appropriate for the conditions within the exhaust system.

Ammonia and NOx slip can increase rapidly, so systems that rely on detecting slip to control the dosing can result in significant release of NOx and/or ammonia. A system and method is disclosed that predicts undesirable slip prior to its occurrence, such that the injector 115 can be controlled to adjust the dosing rate to avoid the slip.

An SCR state model is disclosed in U.S. Pat. No. 8,230,677, to Devarakonda et al., which is hereby incorporated by reference. A related model is disclosed in Harsha Shankar Surenahalli, et al, "Extended Kalman Filter Estimator for $NH_3$ Storage, NO, $NO_2$ and $NH_3$ Estimation in a SCR," No. 2013-01-1581, SAE Technical Paper, 2013, which is hereby incorporated by reference.

In a current embodiment, a one-dimensional SCR model incorporates mass transfer for species, mass balance for ammonia storage on the catalyst, and a heat transfer or temperature distribution through the SCR. In a current embodiment the model assumes (i) the gas phase and surface phase temperature and concentrations are the same; (ii) the catalytic reactions occur on catalyst sites from ammonia stored on the site; and (iii) the energy release from the reactions can be ignored. For the mass balance model, two types of sites on the catalyst are considered, sites that adsorb ammonia and participate in the SCR reactions, and sites that adsorb and desorb ammonia, without participating in the SCR reactions.

The mass transfer for species includes adsorption and desorption of ammonia on the catalyst, $NH_3$ oxidation, NOx reduction reactions, NO oxidation, and $N_2$ formation, as outlined below. $NH_3$ adsorbed onto the catalyst may react with NOx on the catalyst surface to form $N_2$ and $H_2O$, or it may desorb back into the exhaust stream without reacting. Equations (1)-(4) below represent ammonia adsorption and desorption on catalyst sites $S_1$ that adsorb $NH_3$ and participate in SCR reactions, and sites $S_2$ that adsorb and desorb $NH_3$ without participating in SCR reactions. The adsorbed ammonia is indicated with a star superscript:

$$NH_3 + S_1 \rightarrow NH_{3,1}^* \tag{1}$$

$$NH_3 + S_2 \rightarrow NH_{3,2}^* \tag{2}$$

$$NH_{3,1}^* \rightarrow S_1 + NH_3 \tag{3}$$

$$NH_{3,2}^* \rightarrow S_2 + NH_3 \tag{4}$$

Oxidation of ammonia is modeled by equation (5):

$$4NH_{3,1}^* + 3O_2 \rightarrow 2N_2 + 6H_2O \tag{5}$$

NOx reduction reactions (occurring on sites $S_1$) are modeled by equations (6)-(9), and are sometimes referred to as the std1, std2, fast, and slow reactions, respectively:

$$4NH_{3,1}^* + 4NO + O_2 \rightarrow 4N_2 + 6H_2O \tag{6}$$

$$5NH_{3,1}^* + 3NO + 9/4O_2 \rightarrow 4N_2 + 15/2H_2O \tag{7}$$

$$4NH_{3,1}^* + 2NO + 2NO_2 \rightarrow 4N_2 + 6H_2O \tag{8}$$

$$4NH_{3,1}^* + 3NO_2 \rightarrow 7/2N_2 + 6H_2O \tag{9}$$

NO oxidation and $N_2O$ formation are represented by equations (10) and (11), respectively:

$$2NO + O_2 \rightarrow 2NO_2 \tag{10}$$

$$6NH_{3,1}^* + 8NO_2 \rightarrow 7N_2O + 9H_2O \tag{11}$$

Species mass transfer equations are represented generically by equation (12):

$$\frac{\partial C_i}{\partial t} = -V\frac{\partial C_i}{\partial x} + \sum n_j R_j \tag{12}$$

where V is the velocity (or speed) of the exhaust gas, i indexes the species $NH_3$, NO, $NO_2$ and $N_2O$, n is the stoichiometric constant, $R_j$ is the reaction rate (gmole/m$^3$-s), and j indexes the corresponding reaction equation (Eqs. (1)-(11)). Therefore, the species mass transfer equations may be written:

$$\frac{\partial C_{NH_3}}{\partial t} = -V\frac{\partial C_{NH_3}}{\partial x} - (R_{ads1} - R_{des1} + R_{ads2} - R_{des2}) \tag{13}$$

$$\frac{\partial C_{NO}}{\partial t} = -V\frac{\partial C_{NO}}{\partial x} - (4R_{Std1} + 2R_{Fast} + 3R_{Std2} + 2R_{NO}) \tag{14}$$

$$\frac{\partial C_{NO_2}}{\partial t} = -V\frac{\partial C_{NO_2}}{\partial x} - (2R_{Fast} + 3R_{slow} - 2R_{NO} + 8R_{N_2O}) \tag{15}$$

$$\frac{\partial C_{N_2O}}{\partial t} = -V\frac{\partial C_{N_2O}}{\partial x} - (7R_{N_2O}) \tag{16}$$

A mass balance model accounts for the ammonia storage by the catalyst. Define $\theta$ as the ammonia storage fraction at a given site, and $\omega$ as the maximum storage capacity, then for sites that do not participate in the SCR NOx reduction reactions, $$\omega_2 \cdot \dot{\theta}_2 = R_{ads2} - R_{des2} \tag{17}$$

and for sites that do participate in the SCR reactions, $$\omega_1 \cdot \dot{\theta}_1 = R_{ads1} - R_{des1} - 4R_{NH_3,Ox} - 4R_{std1}$$

$$-5R_{std\,2} - 4R_{Fast} - 4R_{slow} - 4R_{N_2O} \tag{18}$$

The reaction rates $R_j$ may be modeled as a function of temperature, using the well-known Arrhenius equation, $k_j = A_j * \exp(E_{a,j}/RT)$, then:

$$R_{ads1} = k_{ads1} \cdot C_{NH_3} \cdot (1-\theta_1) \cdot \omega_1$$

$$R_{ads2} = k_{ads2} \cdot C_{NH_3} \cdot (1-\theta_2) \cdot \omega_2$$

$$R_{des1} = k_{des1} \cdot \theta_1 \cdot \omega_1$$

$$R_{des2} = k_{des2} \cdot \theta_2 \cdot \omega_2$$

$$R_{NH_3,Ox} = k_{NH_3,Ox} \cdot y_{O_2} \cdot \theta_1 \cdot \omega_1$$

$$R_{NO,Ox} = k_{NO,Ox} \left( C_{NO} \cdot \sqrt{y_{O_2}} - \frac{C_{NO_2}}{k_p} \right)$$

$$R_{std1} = k_{std1} \cdot C_{NO} \cdot y_{O_2} \cdot \theta_1 \cdot \omega_1$$

$$R_{std2} = k_{std2} \cdot C_{NO} \cdot y_{O_2} \cdot \theta_1 \cdot \omega_1$$

$$R_{fast} = k_{fast} \cdot C_{NO} \cdot C_{NO_2} \cdot \theta_1 \cdot \omega_1$$

$$R_{slow} = k_{slow} \cdot C_{NO_2} \theta_1 \cdot \omega_1$$

where $y_{O_2}$ is the mass fraction of oxygen, and $k_p$ is the thermodynamic equilibrium constant.

The temperature distribution in the SCR may be modeled in a number of different ways. For example, the heat transfer equation applied to honeycomb substrates may be written as:

$$(\rho_w C_w + \rho_{exh} C_v) \frac{\partial T}{\partial t} = -\rho_{exh} V C_p \frac{\partial T}{\partial x} - h_a \frac{4 a_w}{a_p^2 - a_w^2} (T - T_a) \quad (19)$$

wherein the change in the internal energy (right-hand side of the equations) comprises a conduction term and a convention term.

In order to simplify the numerical analysis to provide more timely feedback for controlling dosing in the SCR system, the controlling equations may be further simplified. For example, in one embodiment the heat equation is simplified to correspond to one-dimensional conduction in a rod. Another simplifying approach is to measure the inlet and outlet temperatures, and interpolate a temperature profile between the measured temperatures.

To greatly simplify the governing equations, the species mass transfer equations (13)-(16) may be written in steady form, e.g., assume that the catalyst fills with the respective species instantaneously. In a current embodiment the simplified model equations are:

$$T(x) = T_1 + \frac{T_2 - T_1}{L} x$$

$$\omega_2 \cdot \theta_2 = R_{ads2} - R_{des2}$$

$$\omega_1 \cdot \theta_1 = R_{ads1} - R_{des1} - 4R_{NH_3,Ox} - 4R_{Std1} - 5R_{std2} - 4R_{Fast} - 4R_{slow} - 6R_{N_2O}$$

$$V \frac{\partial C_{NH_3}}{\partial x} = -(R_{ads1} - R_{des1} + R_{ads2} - R_{des2})$$

$$V \frac{\partial C_{NO}}{\partial x} = -(4R_{Std1} + 2R_{Fast} + 3R_{Std2} + 2R_{NO})$$

$$V \frac{\partial C_{NO_2}}{\partial x} = -(2R_{Fast} + 3R_{slow} - 2R_{NO} + 8R_{N_sO})$$

$$V \frac{\partial C_{N_2O}}{\partial x} = -(7R_{N_2O})$$

For this one-dimensional model the exhaust velocity, V, may be modeled as the inlet velocity scaled by the relevant flow area through the SCR system, for example. In another embodiment, the model may assume a uniform velocity through the SCR system.

A test bed comprising an engine 90 with an SCR system 110 as shown in FIG. 1, was operated for 2,400 seconds in accordance with the ramped-modal cycle (RMC) specified in 40 CFR 86, "Control of Emissions From New and In-Use Highway Vehicles and Engines." A sensor 112 at the inlet measured the NOx in the exhaust stream 92, and the dosing injector 115 was operated to inject urea to produce a selectable ammonia-to-NOx ratio. Inlet and outlet temperatures, the ammonia concentration, and the NOx concentration at the outlet of the SCR system 110 were also measured. The one-dimensional, steady model described above was then used to simulate the test bed under the same applied load conditions.

Figure 3A:
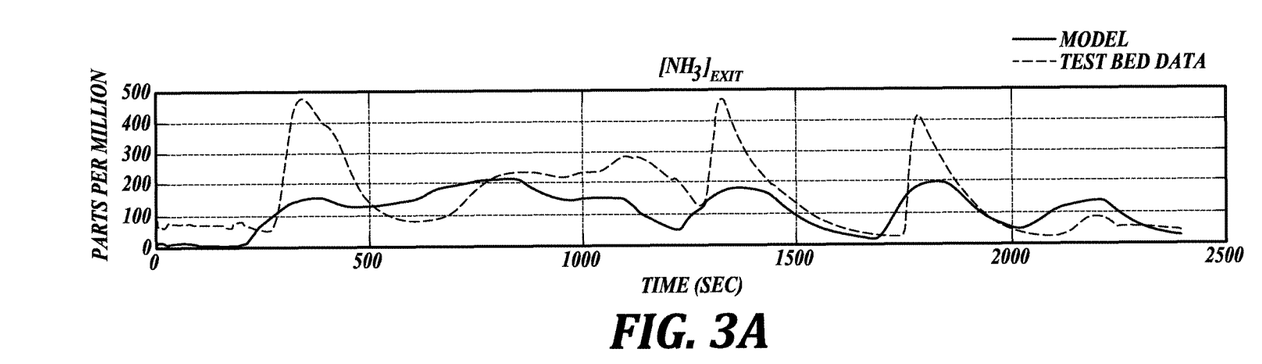
FIG. 3A is a time plot comparing the ammonia concentration measured at the outlet of a selective catalytic reduction (SCR) system of a diesel engine test bed running the ramped-modal-cycle (RMC) test procedure with reductant dosing controlled to produce an inlet ammonia:NOx ratio of 1.3, and the corresponding ammonia concentration predicted by a state model of the system in accordance with the present invention.
Figure 3B:
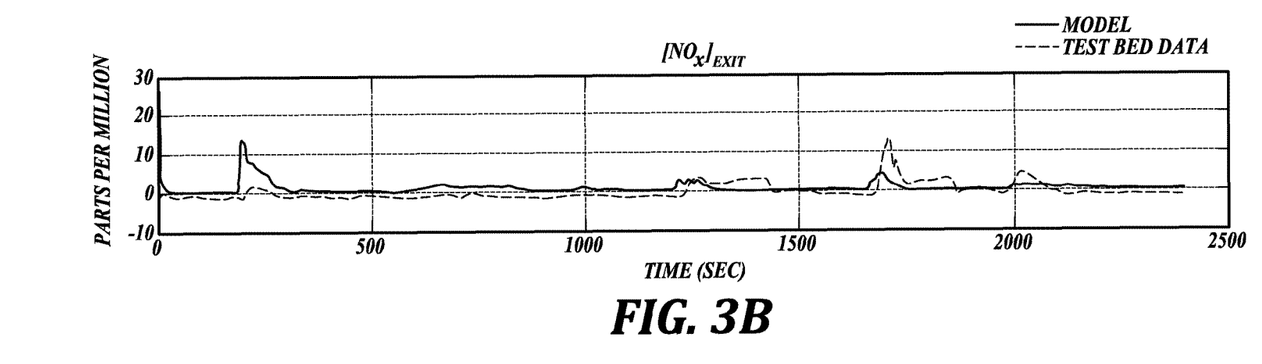
FIG. 3B is a time plot comparing the corresponding NOx concentration measured at the outlet of the SCR system with the calculated NOx concentration.

To test the ability of the model to predict ammonia slip, the test bed and model were run with the urea injector controlled to produce an ammonia-to-NOx ratio (ANR) of 1.3 at the inlet. FIG. 3A shows the measured (dashed line) and calculated (solid line) ammonia concentrations at the SCR system 110 outlet as a function of time. FIG. 3B shows the measured and calculated NOx concentration at the SCR system 110 outlet as a function of time. Because of the relatively high dosing level, we expect significant ammonia slip.

FIG. 3A shows abrupt increases in the measured concentration of ammonia at the exit to the SCR system (i.e., ammonia slip) occur at approximately 275 seconds, 1,300 seconds, and at 1,750 seconds. Remarkably, the model predicts abrupt increases in the concentration of ammonia at the exit to the SCR system at approximately 200 seconds, 1230 seconds, and 1690 seconds. In each instance, the model predicts the increased ammonia slip approximately one minute before the increased slip occurs in the test bed. The results from the model, therefore, may be used to adjust the operation of the dosing injector (i.e., reducing the rate of ammonia injection) before ammonia slip begins to completely avoid or significantly reduce ammonia slip.

FIG. 3B compares the measured test bed NOx concentration (ppm) at the SCR system outlet for 2,400 seconds of operation (dashed line) with the NOx concentration calculated using the model (solid line). As would be expected, with an ANR of 1.3 very little NOx slip is detected or measured.

Figure 4A:
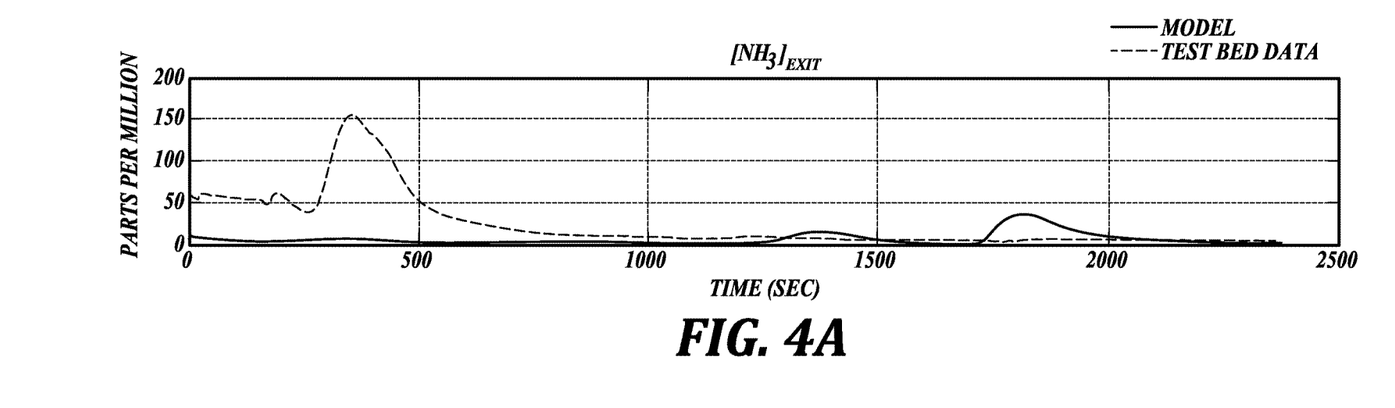
FIG. 4A is a time plot comparing the ammonia concentration measured at the outlet of the SCR system of the diesel engine test bed running the RMC test procedure with reductant dosing controlled to produce an inlet ammonia: NOx ratio of 1.0, and the corresponding ammonia concentration predicted by a state model of the system in accordance with the present invention.
Figure 4B:
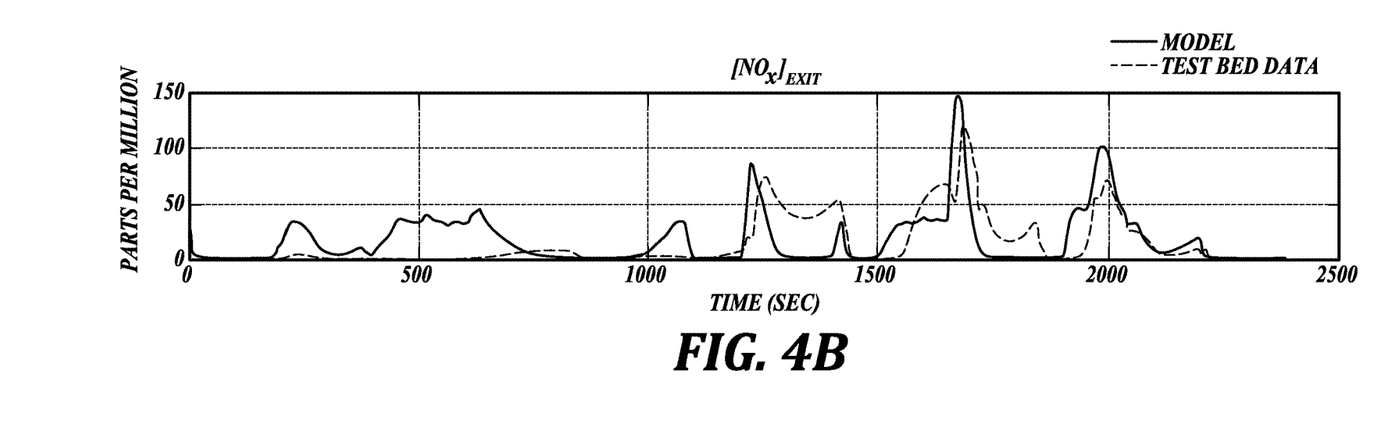
FIG. 4B is a time plot comparing the corresponding NOx concentration measured at the outlet of the SCR system with the calculated NOx concentration.

To test the ability of the model to predict NOx slip, the test bed and model were run with the urea injector controlled to produce an ANR of 1.0 at the inlet. FIGS. 4A and 4B show measured and calculated ammonia and NOx concentrations at the SCR system outlet, as a function of time.

FIG. 4A compares the measured test bed ammonia concentration (ppm) at the SCR system outlet for 2,400 seconds of operation (dashed line) with the ammonia concentration calculated using the model (solid line). As expected, the lower dosing rate (ANR) produces very little ammonia slip. The minor test bed data ammonia slip at about 350 seconds is believed to be related to startup conditions, which are not included in the model at this time.

FIG. 4B, however, compares the measured test bed NOx concentration (ppm) at the SCR system outlet for 2,400 seconds of operation (dashed line) with the NOx concentration calculated using the model (solid line). Abrupt increases in the measured concentration of NOx at the exit to the SCR system (i.e., NOx slip) occurred at approximately 1,225 seconds, 1,550 seconds, 1,675 seconds, and 1,940 seconds. Remarkably, abrupt increases in the predicted concentration of NOx at the exit to the SCR system are predicted by the model to occur at approximately 1,225 seconds, 1,500 seconds, 1,650 seconds, and 1,910 seconds. The model predicts NOx slip increases approximately one-half minute before the increased slip occurs in the test bed. The results from the model, therefore, may be used to adjust the operation of the dosing injector (i.e., increasing the rate of ammonia injection) before NOx slip begins to completely avoid or significantly reduce NOx slip.

Similar predictive results were obtained when comparing measured concentrations of NO with calculated concentrations of NO at the SCR system outlet, and when comparing measured concentrations of NO2 with calculated concentrations of NO2 at the SCR system outlet.

The model was found to similarly anticipate ammonia slip and NOx slip using the more transient Federal Test Procedure (FTP), specified in 40 CFR 86.

Figure 5A:
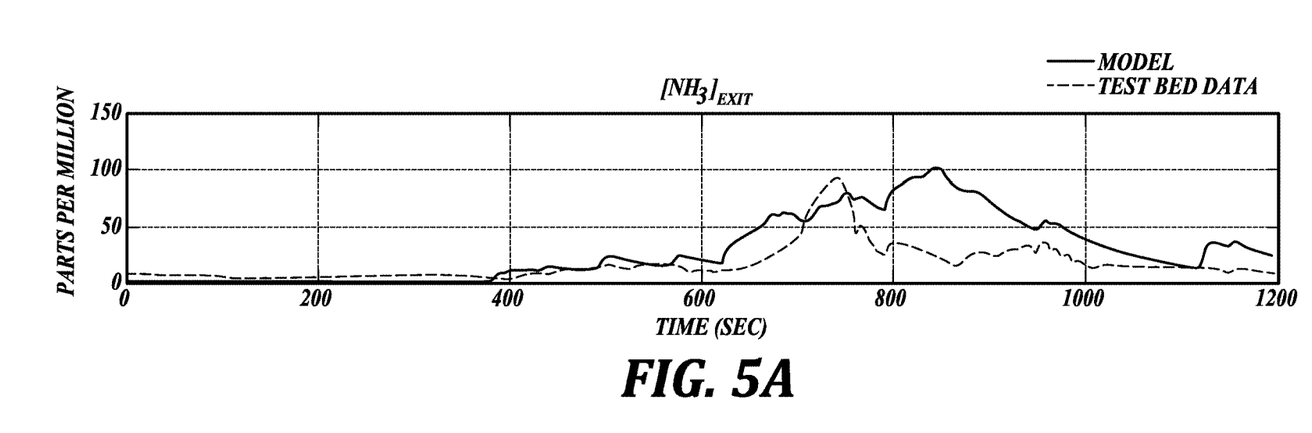
FIG. 5A is a time plot comparing the ammonia concentration measured at the outlet of a selective catalytic reduction (SCR) system of a diesel engine test bed running the Federal Test Procedure (FTP) with reductant dosing controlled to produce an inlet ammonia:NOx ratio of 1.1, and the corresponding ammonia concentration predicted by a state model of the system in accordance with the present invention.
Figure 5B:
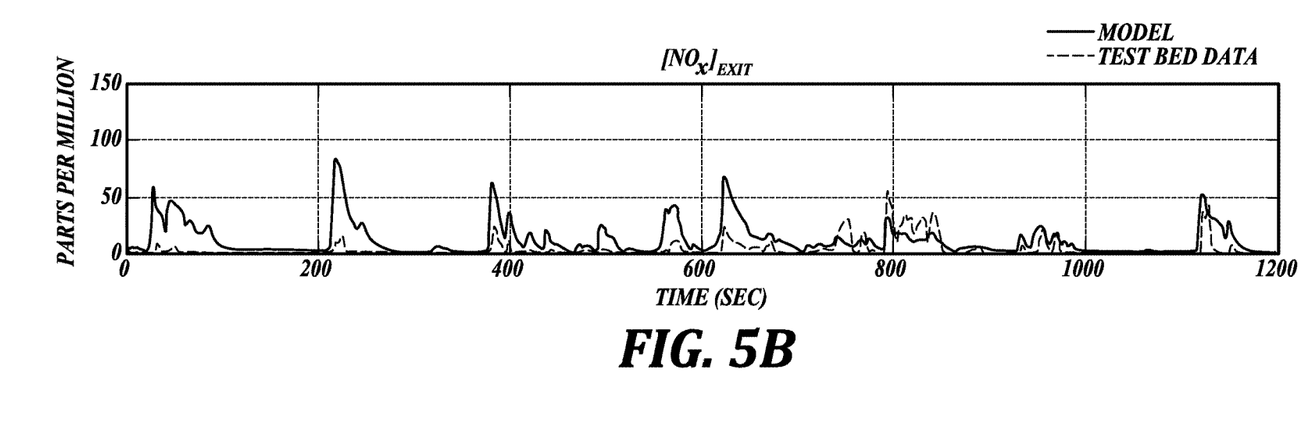
FIG. 5B is a time plot comparing the corresponding NOx concentration measured at the outlet of the SCR system with the calculated NOx concentration.

Similar to the tests discussed above, the test bed was operated for 1,200 seconds in accordance with the FTP profile with the urea injector controlled to produce an ammonia-to-NOx ratio (ANR) of 1.1 at the inlet. FIG. 5A shows the measured (dashed line) and calculated (solid line) ammonia concentrations at the SCR system 110 outlet as a function of time. FIG. 5B shows the measured and calculated NOx concentration at the SCR system 110 outlet as a function of time.

FIG. 5A shows a relatively rapid increase in the measured concentration of ammonia at the exit to the SCR system (i.e., ammonia slip) beginning at approximately 650 seconds. The model predicts the increase in the concentration of ammonia at the exit at about 625 seconds. The model predicts the increased ammonia slip approximately 25 seconds before the increased slip occurs in the test bed. The results from the model, therefore, may be used to adjust the operation of the dosing injector before ammonia slip begins to completely avoid or significantly reduce ammonia slip.

Although relatively small NOx slip occurred in this test, FIG. 5B shows the model (solid line) generally anticipates even the lower levels of NOx slip during the test.

Figure 6:
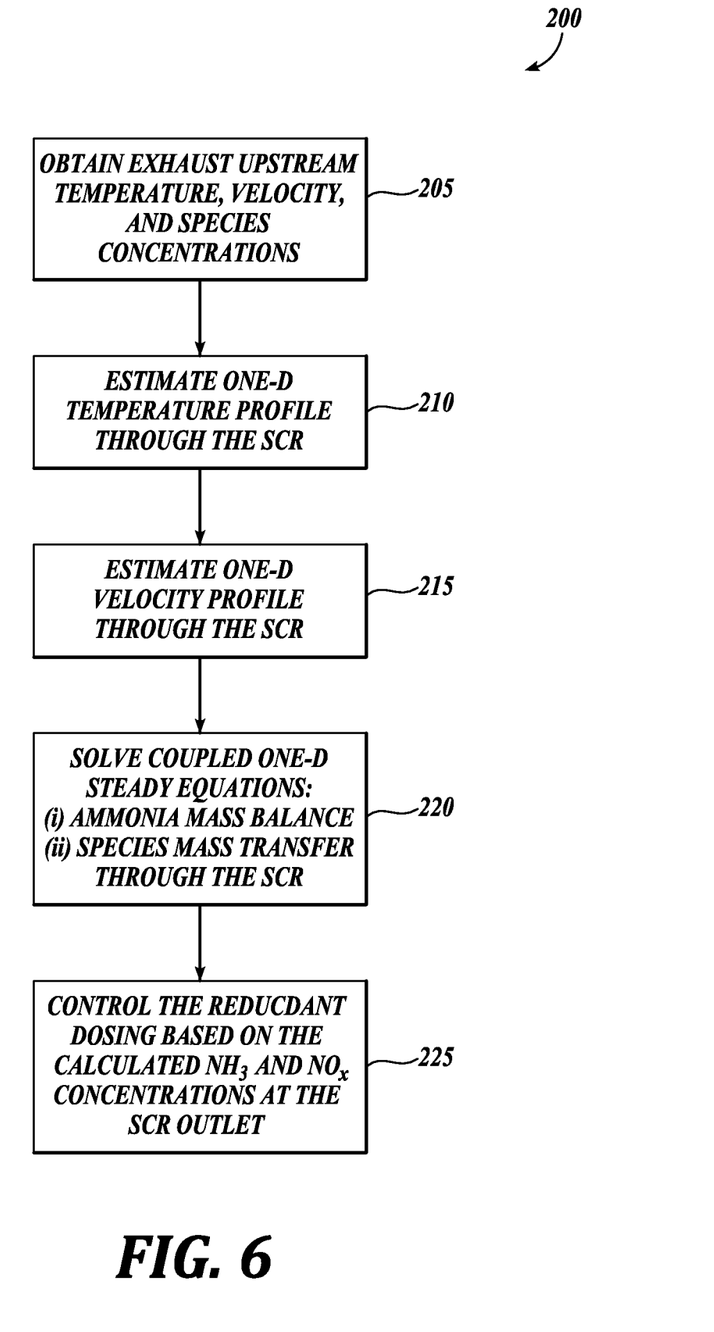
FIG. 6 illustrates a method for controlling the dosing in an SCR system in accordance with the present invention.

A method for controlling the reductant dosing rate 200 is shown in FIG. 6. The upstream exhaust temperature, velocity or flow rate, and species concentrations are obtained 210. The upstream temperature may be obtained, for example, from the upstream sensor module 112 (FIG. 2). For example, the upstream sensor module 112 may include a temperature sensor, a flow rate sensor, and one or more NOx sensors. Alternatively, one or more of these upstream parameters may be obtained from a lookup table or calculated based on other known engine operating conditions.

A one-dimensional gas temperature profile through the SCR system 110 is estimated 215, and a one-dimensional gas velocity profile is estimated 220 by the controller 120. For example, the one-dimensional gas temperature profile may be estimated by measuring the inlet and outlet temperatures, and interpolating between the measured temperatures. In another embodiment, a one-dimensional heat equation may be used to estimate the temperature through the SCR system 110. For example, the one-dimensional gas velocity profile may be calculated based on a gas velocity measured upstream of the SCR catalyst and the geometry of the SCR system 100. Optionally, the gas velocity profile calculation may additionally factor in the calculated temperature profile.

The controller 120 then solves a coupled set of one-dimensional, steady equations that model ammonia mass balance, and the species mass transfer through the SCR is then solved 225, to determine the downstream ammonia and NOx concentrations. Suitable equations are discussed above.

The controller 120 then uses the calculated downstream ammonia and NOx concentrations to control the injector 115, e.g., by adjusting the rate of injection of reductant into the SCR system 110. Alternatively, the controller 120 may use the rate of change in the calculated downstream ammonia and NOx concentrations to control the injector 115. For example, if the model predicts a rapid increase in ammonia concentration at the outlet, the controller 120 may control the injector 115 to reduce the flow of reductant into the SCR system. Alternatively, if the model predicts a rapid increase in NOx concentration at the outlet, the controller may control the injector 115 to increase the flow of reductant into the SCR system.

It is contemplated that the controller 120 may continuously adjust the injector 115 based on the calculated outlet ammonia and NOx concentrations. For example, the rate of injection may be related to a linear combination of the ammonia concentration and the NOx concentration at the outlet. In another embodiment the injection rate may be adjusted periodically, for example, once every second. It is contemplated that conventional heuristically determined lookup tables, or the like, may be used by the controller 120 to determine a reductant flow rate based on the calculated outlet ammonia and NOx concentrations.

While illustrative embodiments have been illustrated and described, it will be appreciated that various changes can be made therein without departing from the spirit and scope of the invention.

The embodiments of the invention in which an exclusive property or privilege is claimed are defined as follows:

1. A method for controlling reductant dosing to an exhaust stream for a selective catalytic reduction (SCR) system having an inlet, an outlet, an SCR catalyst, a controllable reductant injector, a reservoir of reductant fluidly connected to the reductant injector, and a controller in signal communication with the reductant injector, the method comprising:
   obtaining an exhaust stream temperature upstream of the SCR catalyst;
   obtaining a speed of the exhaust stream entering the SCR system;
   obtaining a concentration of one or more nitrogen oxides entering the SCR system; and
   with the controller:
   (i) calculating a one-dimensional temperature profile and a one-dimensional exhaust stream velocity profile through the SCR system using the exhaust stream temperature entering the SCR system and the speed of the exhaust stream entering the SCR system;
   (ii) solving a set of coupled equations comprising (a) one-dimensional, steady ammonia mass balance equations and (b) one-dimensional, steady species mass transfer equations, to calculate a one-dimensional distribution of ammonia storage in the catalyst and a one-dimensional distribution of exhaust species concentrations through the SCR system including a concentration of ammonia and a concentration of one or more nitrogen oxides at the SCR outlet; and (iii) controlling the reductant injector, wherein the injector is controlled based on the calculated concentration of ammonia and the calculated concentration of one or more nitrogen oxides at the SCR outlet.

2. The method of claim 1, wherein the upstream exhaust stream temperature is obtained from a first sensor module in the exhaust stream.

3. The method of claim 2, further comprising obtaining a downstream exhaust stream temperature from a second sensor module, wherein the one-dimensional temperature profile is calculated by interpolating between the upstream exhaust stream temperature and the downstream exhaust stream temperature.

4. The method of claim 1, wherein the one-dimensional exhaust stream temperature profile is obtained by solving a one-dimensional energy equation.

5. The method of claim 1, wherein the concentration of nitrogen oxides entering the SCR system is obtained from a sensor module in the exhaust stream upstream of the SCR catalyst.

6. The method of claim 5, wherein the sensor module measures the concentration of a plurality of nitrogen oxides.

7. The method of claim 5, wherein the sensor module measures a concentration of NO and $NO_2$.

8. The method of claim 1, wherein the speed of the exhaust stream entering the SCR system is calculated from an exhaust flow rate and the exhaust stream temperature upstream of the SCR catalyst.

9. The method of claim 1, wherein the one-dimensional, steady ammonia mass balance equations model adsorption, desorption, and storage of ammonia on the SCR catalyst.

10. The method of claim 1, wherein the controller controls the reductant injector also based on the rate of change of the calculated concentration of ammonia and the calculated concentration of one or more nitrogen oxides at the SCR outlet.

11. A system for controlling the dosing of reductant in a selective catalytic reduction (SCR) system for a diesel engine, comprising:
 a chamber having an inlet and an outlet;
 an SCR catalyst disposed in the chamber;
 a controllable injector configured to inject reductant into the chamber;
 a reservoir for SCR reductant fluidly connected to the injector;
 an upstream sensor module positioned to intercept an exhaust stream from the diesel engine upstream of the chamber;
 a controller in signal communication with the upstream sensor module and with the injector, wherein the controller is configured to:
  (i) receive an upstream exhaust stream temperature and a concentration of one or more nitrogen oxides in the exhaust stream from the upstream sensor module;
  (ii) calculate a speed of the exhaust stream entering the SCR system;
  (iii) calculate a one-dimensional temperature profile and a one-dimensional exhaust stream velocity profile through the SCR system using the exhaust stream temperature entering the SCR system and the speed of the exhaust stream entering the SCR system;
  (iv) solve a set of coupled equations comprising (a) one-dimensional, steady ammonia mass balance equations and (b) one-dimensional, steady species mass transfer equations, to calculate a one-dimensional distribution of ammonia storage in the catalyst and a one-dimensional distribution of exhaust species concentrations through the SCR system including a concentration of ammonia and a concentration of one or more nitrogen oxides at the SCR outlet; and
  (v) control the reductant injector, wherein the injector is controlled based on the calculated concentration of ammonia and the calculated concentration of one or more nitrogen oxides at the SCR outlet.

12. The system of claim 11, wherein the upstream sensor module is disposed at the inlet to the chamber.

13. The system of claim 12, further comprising a downstream sensor module disposed at the outlet to the chamber and is in signal communication with the controller, wherein the controller obtaining a downstream exhaust stream temperature from the downstream sensor module, and wherein the controller calculates the one-dimensional temperature profile by interpolating between the upstream exhaust stream temperature and the downstream exhaust stream temperature.

14. The system of claim 11, wherein the one-dimensional exhaust stream temperature profile is obtained by solving a one-dimensional energy equation.

15. The system of claim 11, wherein the upstream sensor module measures the concentration of a plurality of nitrogen oxides.

16. The system of claim 11, wherein the upstream sensor module measures a concentration of NO and $NO_2$.

17. The system of claim 11, wherein the speed of the exhaust stream entering the SCR system is calculated from an exhaust flow rate and the upstream exhaust stream temperature.

18. The system of claim 11, wherein the one-dimensional, steady ammonia mass balance equations model adsorption, desorption, and storage of ammonia on the SCR catalyst.

19. The system of claim 11, wherein the controller controls the reductant injector also based on the rate of change of the calculated concentration of ammonia and the calculated concentration of one or more nitrogen oxides at the SCR outlet.

20. The system of claim 11, wherein the selective catalytic reduction (SCR) system is configured to be installed on the diesel engine of a Class 8 truck.

* * * * *